(12) United States Patent
Joshi et al.

(10) Patent No.: US 9,834,557 B2
(45) Date of Patent: *Dec. 5, 2017

(54) PROCESS FOR PREPARATION OF (2S, 5R)-7-OXO-6-SULPHOOXY-2-[((3R)-PIPERIDINE-3-CARBONYL)-HYDRAZINO CARBONYL]-1,6-DIAZA-BICYCLO [3.2.1]-OCTANE

(71) Applicant: WOCKHARDT LIMITED, Aurangabad (IN)

(72) Inventors: Sanjeev Joshi, Aurangabad (IN); Karuna Suresh Wankhede, Aurangabad (IN); Sunil Bhaginath Jadhav, Ahmednagar (IN); Shivaji Sampatrao Pawar, Aurangabad (IN); Vinod Kashinath Ahirrao, Aurangabad (IN); Satish Bhawsar, Aurangabad (IN); Prasad Keshav Deshpande, Aurangabad (IN); Ravindra Dattatraya Yeole, Aurangabad (IN); Mahesh Vithalbhai Patel, Aurangabad (IN)

(73) Assignee: WOCKHARDT LIMITED, Chikalthana, Aurangabad (IN)

(*) Notice: Subject to any disclaimer, the term of this patent is extended or adjusted under 35 U.S.C. 154(b) by 0 days.

This patent is subject to a terminal disclaimer.

(21) Appl. No.: 15/472,694

(22) Filed: Mar. 29, 2017

(65) Prior Publication Data

US 2017/0197963 A1 Jul. 13, 2017

Related U.S. Application Data

(63) Continuation of application No. 14/769,815, filed as application No. PCT/IB2013/059326 on Oct. 12, 2013, now Pat. No. 9,657,021.

(30) Foreign Application Priority Data

Mar. 8, 2013 (IN) .......................... 717/MUM/2013

(51) Int. Cl.
$C07D\ 515/02$ (2006.01)
$C07D\ 471/08$ (2006.01)

(52) U.S. Cl.
CPC ........ $C07D\ 471/08$ (2013.01); $C07B\ 2200/13$ (2013.01)

(58) Field of Classification Search
CPC .......................... C07D 471/08; C07B 2200/13
(Continued)

(56) References Cited

U.S. PATENT DOCUMENTS 8,822,450 B2  9/2014 Patel et al.
8,853,197 B1  10/2014 Patel et al.
(Continued)

FOREIGN PATENT DOCUMENTS

WO  WO/2009/091856  7/2009
WO  WO/2012/086241  6/2012
WO  WO/2013/030733  3/2013

OTHER PUBLICATIONS

Valeur et al., Amide bond formation: beyond the myth of coupling reagants.Chem Soc Rev. Feb. 2009;38(2):606-31. doi: 10.1039/b701677h. Epub Dec. 4, 2008.
(Continued)

Primary Examiner — T. Victor Oh
(74) Attorney, Agent, or Firm — Bio Intellectual Property Services LLC (BioIPS); O. (Sam) Zaghmout

(57) ABSTRACT

A process for preparation of (2S, 5R)-7-oxo-6-sulphooxy-2-[((3R)-piperidine-3-carbonyl)-hydrazino carbonyl]-1,6-diaza-bicyclo[3.2.1]octane is disclosed.

6 Claims, 1 Drawing Sheet

(58) Field of Classification Search
USPC .......................................................... 546/121
See application file for complete search history.

(56) References Cited

U.S. PATENT DOCUMENTS

| | | |
|---|---|---|
| 8,987,297 B2 | 3/2015 | Patel et al. |
| 9,132,133 B2 | 9/2015 | Patel et al. |
| 9,381,200 B2 | 7/2016 | Patel et al. |
| 9,393,239 B2 * | 7/2016 | Maiti .................... C07D 519/00 |
| 9,657,021 B2 * | 5/2017 | Joshi ..................... C07D 471/08 |
| 2016/0340359 A1 | 11/2016 | Joshi et al. |

OTHER PUBLICATIONS

Peterson et al., Iterative High-Throughput Polymorphism Studies on Acetaminophen and an Experimentally Derived Structure for Form IIIAm. Chem. Soc., 124, 10958-10959, 10958 (2002).

Morissette et al., High-throughput crystallization: Polymorphs, salts, co-crystals and solvates of pharmaceutical solidsAdvanced Drug Delivery Reviews, 56, 275-300, 296 (2004).

Buar et al., Disappearing Polymorphs Revisited (pp. 6972-6993)Angew. Chem. Int. Ed., 54, 6972-6993 (2015).

* cited by examiner

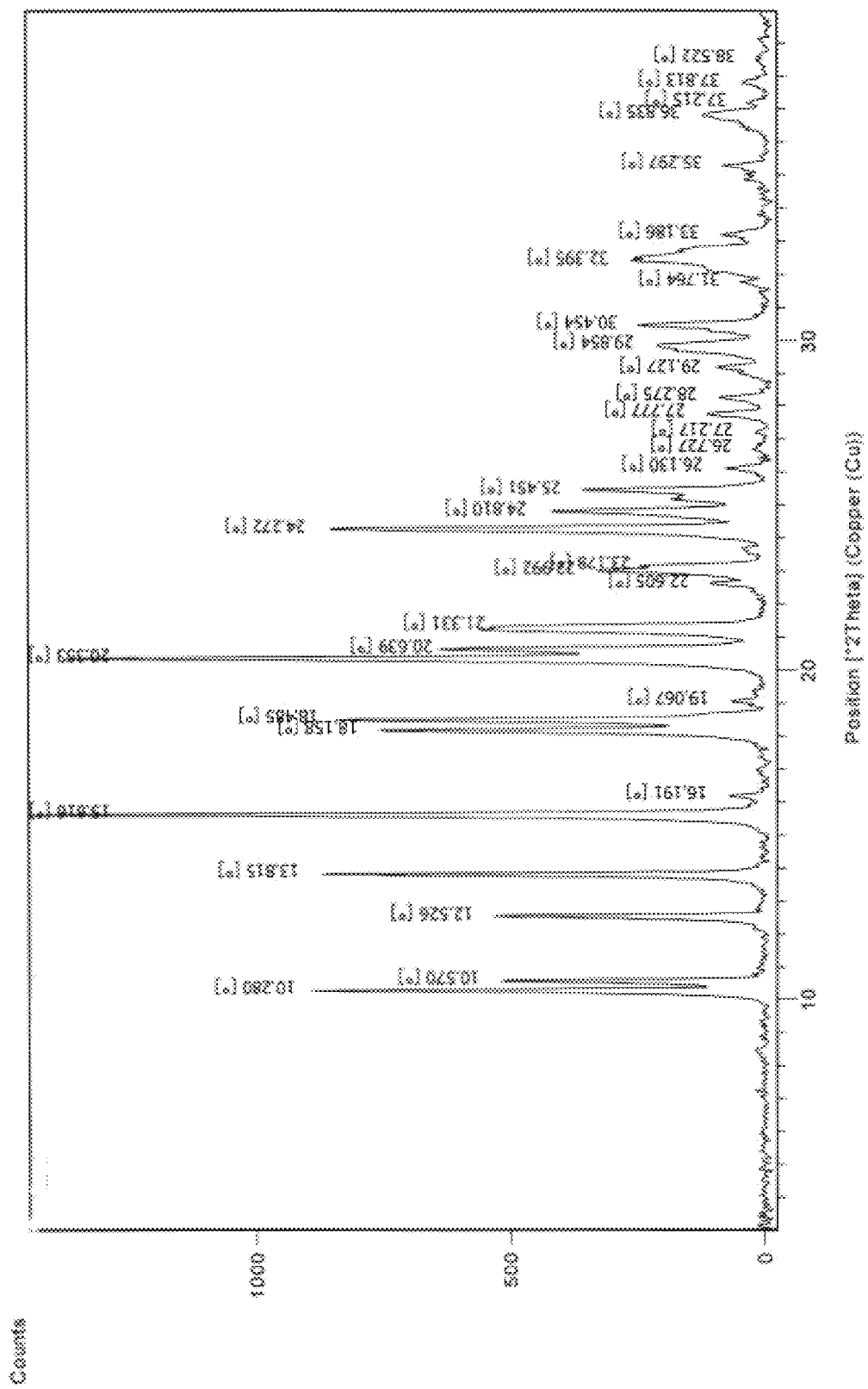

PROCESS FOR PREPARATION OF (2S, 5R)-7-OXO-6-SULPHOOXY-2-[((3R)-PIPERIDINE-3-CARBONYL)-HYDRAZINO CARBONYL]-1,6-DIAZA-BICYCLO [3.2.1]-OCTANE

RELATED PATENT APPLICATIONS

This application is a Continuation of U.S. application Ser. No. 14/769,815, filed Aug. 23, 2015, now pending, which entered the National Phase of Serial No. PCT/IB2013/059326, filed Oct. 12, 2013 which claims the benefit of Indian Patent Application No. 717/MUM/2013 filed on Mar. 8, 2013, the disclosures of which are incorporated herein by reference in its entirety as if fully rewritten herein. All references including patents, patent applications, and literature cited in the specification are expressly incorporated herein by reference in their entirety.

FIELD OF THE INVENTION

The invention relates to a process for preparation of (2S, 5R)-7-oxo-6-sulphooxy-2-[((3R)-piperidine-3-carbonyl)-hydrazino carbonyl]-1,6-diaza-bicyclo[3.2.1]octane.

BACKGROUND OF THE INVENTION

A compound of Formula (I), chemically known as (2S, 5R)-7-oxo-6-sulphooxy-2-[((3R)-piperidine-3-carbonyl)-hydrazino carbonyl]-1,6-diaza-bicyclo[3.2.1]octane has antibacterial properties and is disclosed in PCT International Patent Application No. PCT/IB2012/054290.

SUMMARY OF THE INVENTION

In one general aspect, there is provided a process for preparation of a compound of Formula (I), comprising:

Formula (I)

(a) reacting a compound of Formula (II) with a compound of Formula (III) to obtain a compound of Formula (IV);

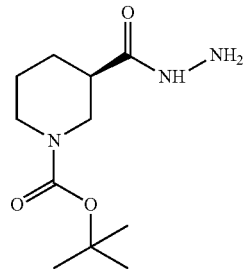
Formula (II)

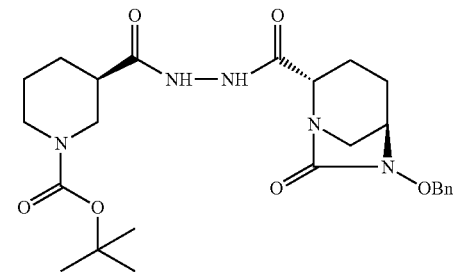
Formula (III)

Formula (IV)

(b) hydrogenolysis of a compound of Formula (IV) to obtain a compound of Formula (V);

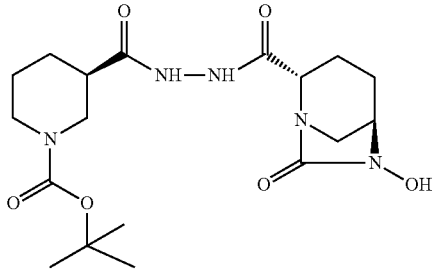
Formula (V)

(c) sulfonating a compound of Formula (V) to obtain a compound of Formula (VI); and

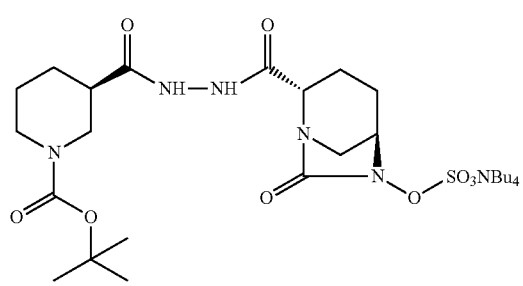
Formula (VI)

(d) converting a compound of Formula (VI) into a compound of Formula (I).

The details of one or more embodiments of the invention are set forth in the description below. Other features, objects and advantages of the invention will be apparent from the following description including claims.

BRIEF DESCRIPTION OF THE DRAWINGS

FIG. 1—X-ray powder diffraction pattern of crystalline form of the compound of Formula (I).

DETAILED DESCRIPTION OF THE INVENTION

Reference will now be made to the exemplary embodiments, and specific language will be used herein to describe the same. It should nevertheless be understood that no limitation of the scope of the invention is thereby intended. Alterations and further modifications of the inventive features illustrated herein, and additional applications of the principles of the invention as illustrated herein, which would occur to one skilled in the relevant art and having possession of this disclosure, are to be considered within the scope of the invention. It must be noted that, as used in this specification and the appended claims, the singular forms "a," "an," and "the" include plural referents unless the content clearly dictates otherwise. All references including patents, patent applications, and literature cited in the specification are expressly incorporated herein by reference in their entirety as if fully rewritten herein.

The term "HOBt" as used herein refers to 1-hydroxybenzotriazole.

The term "EDC" as used herein refers to 1-ethyl-3-(3-dimethylaminopropyl) carbodiimide.

In one general aspect, there is provided a process for preparation of a compound of Formula (I), comprising:

Formula (I)

(a) reacting a compound of Formula (II) with a compound of Formula (III) to obtain a compound of Formula (IV);

Formula (II)

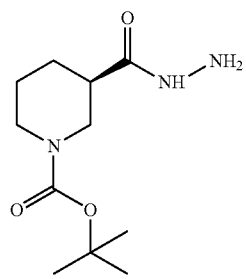

Formula (III)

Formula (IV)

(b) hydrogenolysis of a compound of Formula (IV) to obtain a compound of Formula (V);

Formula (V)

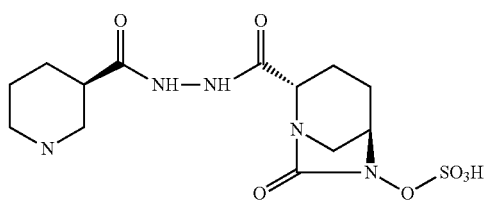

(c) sulfonating a compound of Formula (V) to obtain a compound of Formula (VI); and Formula (VI)

(d) converting a compound of Formula (VI) into a compound of Formula (I).

The compound of Formula (IV) is obtained by reacting a compound of Formula (II) with a compound of Formula (III). In some embodiments, this reaction is carried out in presence of 1-hydroxybenzotriazole. In some other embodiments, the compound of Formula (IV) is obtained by reacting a compound of Formula (II) with a compound Formula (III) in presence of 1-hydroxybenzotriazole and 1-ethyl-3-(3-dimethylaminopropyl)carbodiimide hydrochloride. In some embodiments, this reaction is carried out in water as a reaction solvent.

The compound of Formula (V) is obtained by hydrogenolysis of a compound of Formula (IV). The hydrogenolysis reaction can be carried out using a suitable hydrogenolysis agent. In some embodiments, hydrogenolysis of a compound of Formula (IV) to obtain a compound of Formula (V) is carried out in presence of a transition metal catalyst and a hydrogen source. In some other embodiments, the transition metal catalyst is palladium on carbon and hydrogen source is hydrogen gas. In some other embodiments, the hydrogenolysis reaction is carried out in presence of a suitable solvent such as an alcohol (for example, methanol). In some embodiments, the hydrogenolysis of a compound of Formula (IV) to obtain a compound of Formula (V) is carried out using 10% palladium on carbon catalyst, in presence of hydrogen gas, in methanol as a solvent.

The compound of Formula (VI) is obtained by sulfonating a compound of Formula (V). The sulfonation reaction can be carried out in presence of a suitable solvent. In some embodiments, the sulfonation of a compound of Formula (V) to obtain a compound of Formula (VI) is carried out by reacting a compound of Formula (V) with sulfur trioxide-pyridine complex, followed by treatment with tetra butyl ammonium hydrogen sulfate.

The compound of Formula (VI) is converted to a compound of Formula (I) in presence of a suitable reagent. In some embodiments, the compound of Formula (VI) is converted to a compound of Formula (I) by reacting a compound of Formula (VI) with trifluoroacetic acid.

In some embodiments, the compound of Formula (I) is prepared using a process described in Scheme 1.

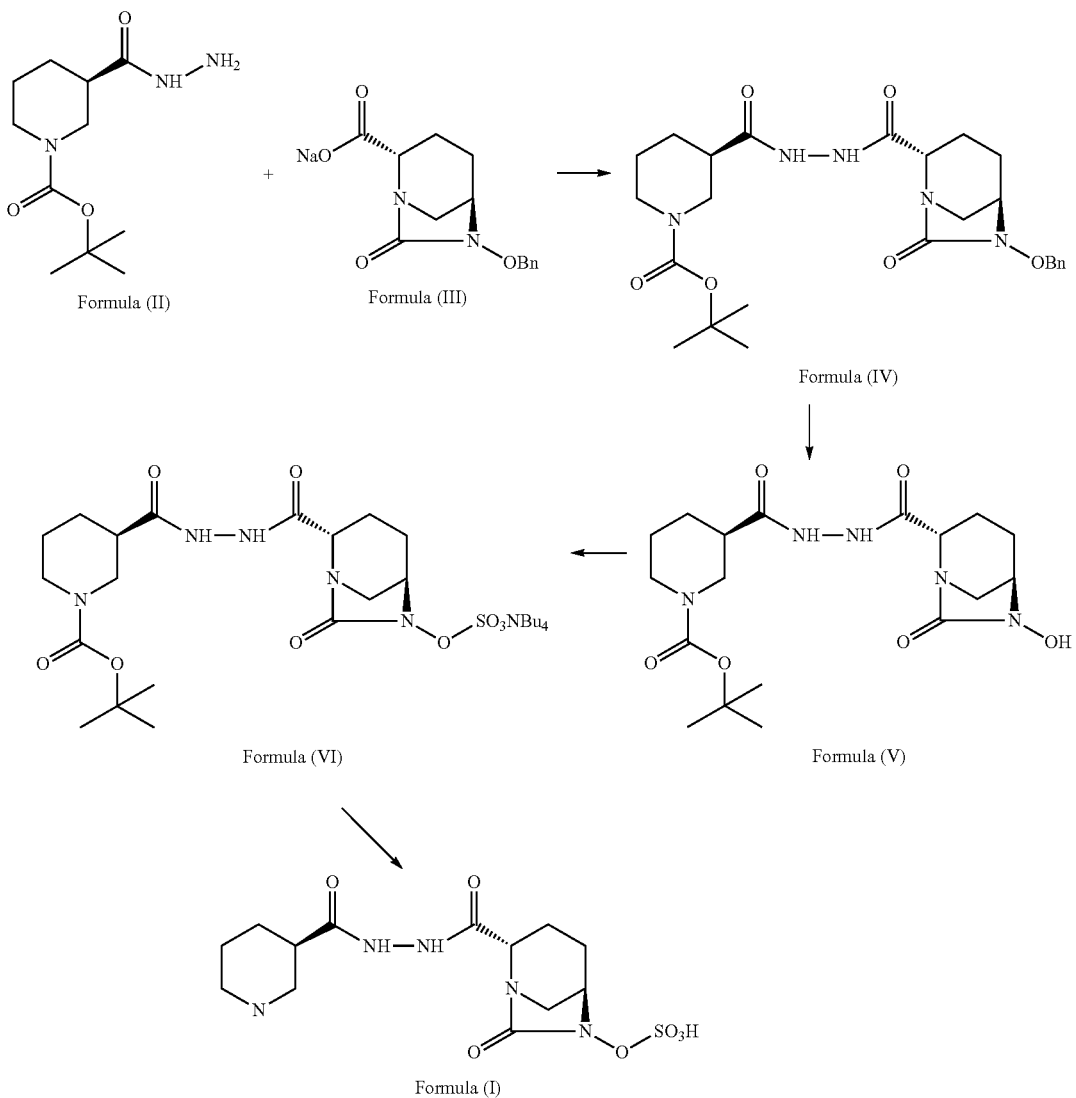

Scheme - 1

In some embodiments, there is provided a compound of Formula (I) in crystalline form.

In some other embodiments, there is a provided a compound of Formula (I) in a crystalline form and having an X-ray powder diffraction pattern comprising a peak selected from the group consisting of 10.28 (±0.2), 10.57 (±0.2), 12.53 (±0.2), 13.82 (±0.2), 15.62 (±0.2), 18.16 (±0.2), 18.49 (±0.2), 20.35 (±0.2), 20.64 (±0.2), 21.33 (±0.2), 22.99

(±0.2), 23.18 (±0.2), 24.27 (±0.2), 24.81 (±0.2), 25.45 (±0.2), 29.85 (±0.2), 30.45 (±0.2), 32.39 (±0.2), and 36.84 (±0.2) degrees 2 theta.

In some other embodiments, there is provided a compound of Formula (I) in a crystalline form and having an X-ray powder diffraction pattern comprising a peak selected from the group consisting of 10.28 (±0.2), 10.57 (±0.2), 12.53 (±0.2), 13.82 (±0.2), 15.62 (±0.2), 18.16 (±0.2), 18.49 (±0.2), 20.35 (±0.2), 20.64 (±0.2), 21.33 (±0.2), 24.27 (±0.2), 24.81 (±0.2), and 25.45 (±0.2) degrees 2 theta.

In some other embodiments, there is provided a compound of Formula (I) in a crystalline form and having an X-ray powder diffraction pattern substantially the same as shown in FIG. 1.

In some embodiments, there is provided a process for the preparation of a compound of Formula (II), comprising:

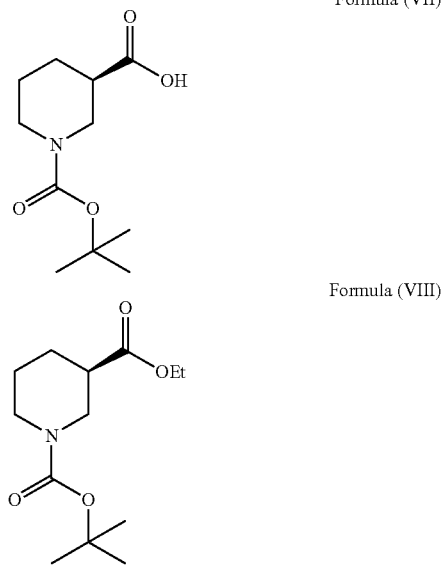

Formula (II)

(a) esterifying a compound of Formula (VII) to a compound of Formula (VIII), and

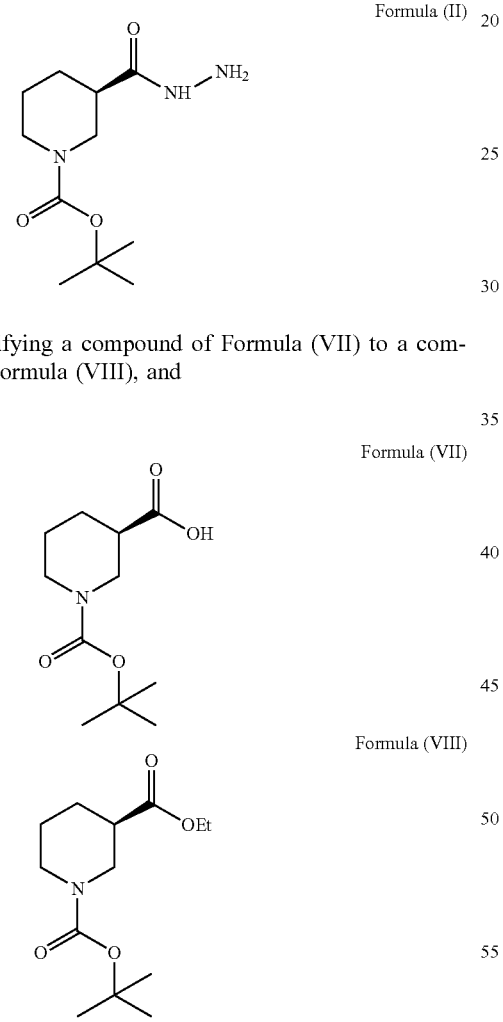

Formula (VII)

Formula (VIII)

(b) converting a compound of Formula (VIII) into a compound of Formula (II).

In general, esterification of a compound of Formula (VII) to a compound of Formula (VIII) can be carried out using a suitable esterification agent. Typical example of a suitable esterification agent includes ethyl iodide in presence of potassium carbonate. The esterified compound of Formula (VIII) is then converted to a compound Formula (II) using a suitable reagent such as hydrazine hydrate. A schematic for synthesis of a compound of Formula (II) is given in Scheme-2.

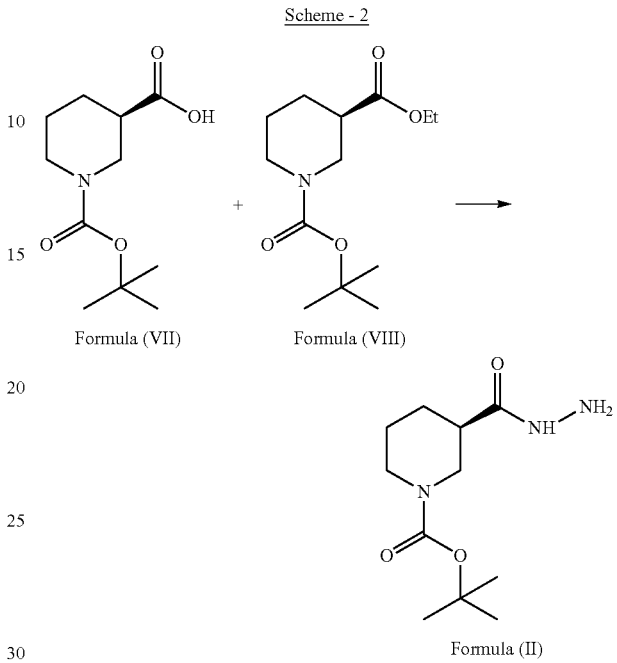

Scheme - 2

Formula (VII)    Formula (VIII)

Formula (II)

It will be readily apparent to one skilled in the art that varying substitutions and modifications may be made to the invention disclosed herein without departing from the scope and spirit of the invention. For example, those skilled in the art will recognize that the invention may be practiced using a variety of different compounds within the described generic descriptions.

EXAMPLES

The following examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

Example-1

Preparation of (R)—N-Boc-piperidine-3-carboxylic acid hydrazide (II)

Step-1: Preparation of (R)-Ethyl-N-Boc-piperidine-3-carboxylate (VIII)

To a solution of (R)—N-Boc-piperidine-3-carboxylic acid (1 kg. 4.36 mol) in N,N-dimethylacetamide (3 L) was charged potassium carbonate (0.664 kg, 4.80 mol) under mechanical stirring and the resulting suspension was stirred for 30 minutes at room temperature. To the reaction mass, ethyl iodide (0.75 kg, 4.80 mol) was charged via addition funnel and the reaction mass was stirred for 15 minutes at room temperature followed by at 50° C. for 1 hour. The reaction was monitored using TLC (ethyl acetate: hexane 1:1). After the reaction was complete, the reaction mass was allowed to cool to room temperature and diluted with ethyl acetate (5 L). The suspension was filtered under suction and the wet cake was washed with ethyl acetate (5 L). The filtrate was stirred with 5% w/v sodium thiosulfate (15 L) and layers were separated. The aqueous layer was re-extracted with additional ethyl acetate (5 L). The combined organic layer was washed with water (5 L) and dried over sodium sulfate. The organic layer was evaporated under vacuum to provide semi-solid which solidifies upon standing as (R)-ethyl-N-Boc-piperidine-3-carboxylate in 1.1 kg quantity in 99.5% yield.

Analysis:
NMR: (CDCl3): 4.63 (q, 2H), 3.90 (d, 1H), 2.87-2.95 (m, 2H), 2.73 (td, 1H), 2.32-2.39 (m, 1H), 1.66-2.01 (m, 2H), 1.52-1.68 (m, 2H), 1.39 (s, 9H), 1.19 (t, 3H).
Mass: (M+1): 258.1 for C13H23NO4;

Step-2: Preparation of
(R)—N-Boc-piperidine-3-carboxylic acid hydrazide
(II)

(R)—N-Boc-ethyl-piperidine-3-carboxylate (1.1 kg, 4.28 mol) was liquefied by warming and transferred to a round bottom flask (10 L), to this was charged hydrazine hydrate (0.470 kg, 9.41 mol) and stirring was started. The reaction mixture was stirred at about 120° C. to 125° C. for 5 hours. As the TLC showed (Chloroform: methanol 9:1) completion of reaction, the reaction mixture was cooled to room temperature and diluted with water (5.5 L) followed by dichloromethane (11 L) and was stirred for 20 minutes. The layers were separated and aqueous layer was extracted with additional dichloromethane (5.5 L). Combined organic layer was washed with water (2.75 L). The organic layer was dried over sodium sulfate and evaporated under vacuum to provide a thick gel which upon stirring and seeding in the presence of cyclohexane (5.5 L) provided white solid. The suspension was filtered and wet cake was washed with fresh cyclohexane (0.5 L). The cake was dried at 35° C. under vacuum to provide (R)—N-Boc-piperidine-3-carboxylic acid hydrazide as a white solid in 0.90 kg quantity in 87% yield.

Analysis
NMR: (CDCl3): 7.42 (br s, 1H), 3.92 (d, 1H), 3.88 (s, 2H), 3.54-3.65 (br s, 1H), 3.17 (br t, 1H), 2.98 (br s, 1H), 2.22-2.32 (br s, 1H), 1.82-1.90 (br m, 2H), 1.76 (s, 1H), 1.60-1.70 (m, 1H), 1.45 (s, 9H).
Mass (M+1): 244.1 for C11H21N3O3.
Specific rotation: $[\alpha]^{25}_D = -53.5°$ (c 0.5, Methanol).
HPLC purity: 99%

Example 2

Preparation of (2S, 5R)-7-oxo-6-sulphooxy-2-[((3R)-piperidine-3-carbonyl)-hydrazinocarbonyl]-1,6-diaza-bicyclo[3.2.1]octane (I)

Step-1: Preparation of (2S, 5R)-6-benzyloxy-7-oxo-2-[((3R)—N-Boc-piperidine-3-carbonyl)-hydrazinocarbonyl]-1,6-diaza-bicyclo[3.2.1]octane(IV)

Sodium (2S, 5R)-7-oxo-6-benzyloxy-1,6-diaza-bicyclo[3.2.1]octane-2-carboxylate (III, 200 gm, 0.67 mol; prepared using a method disclosed in Indian Patent Application No 699/MUM/2013) was dissolved in water (2.8 L) to obtain a clear solution under stirring at room temperature. To the clear solution was added successively, (R)—N-Boc-piperidine-3-carboxylic acid hydrazide (171 gm, 0.70 mol), EDC hydrochloride (193 gm, 1.01 mol), and HOBt (90.6 gm, 0.67 mol) followed by water (0.56 L) under stirring at 35° C. The reaction mixture was stirred at 35° C. for 20 hours. As maximum precipitation was reached, TLC (acetone: hexane 35:65) showed completion of reaction. The suspension was filtered under suction and the wet cake was washed with additional water (2 L). The wet cake was suspended in warm water (10 L) and stirred for 5 hours. It was filtered under suction and dried under vacuum at 45° C. to furnish (2S, 5R)-6-benzyloxy-7-oxo-2-[((3R)—N-Boc-piperidine-3-carbonyl)-hydrazinocarbonyl]-1,6-diaza-bicyclo[3.2.1]octane (IV) as a white powder in 270 gm quantity in 87% yield.

Analysis
NMR: (CDCl3): 8.40 (br s, 1H), 7.34-7.44 (m, 5H), 5.05 (d, 1H), 4.90 (d, 1H), 4.00 (br d, 1H), 3.82 (br s, 1H), 3.30 (br s, 1H), 3.16-3.21 (m, 1H), 3.06 (br d, 1H), 2.42 (br s, 1H), 2.29-2.34 (m, 1H), 1.18-2.02 (m, 4H), 1.60-1.75 (m, 4H), 1.45-1.55 (m, 2H), 1.44 (s, 9H).
Mass: (M+1)=502.1 for C25H35N5O6
HPLC purity: 98.4%

Step-2: Preparation of (2S, 5R)-6-hydroxy-7-oxo-2-[((3R)—N-Boc-piperidine-3-carbonyl)-hydrazinocarbonyl]-1,6-diaza-bicyclo[3.2.1]octane (V)

(2S, 5R)-6-benzyloxy-7-oxo-2-[((3R)—N-Boc-piperidine-3-carbonyl)-hydrazinocarbonyl]-1,6-diaza-bicyclo[3.2.1]octane (153 gm, 0.305 mol) was dissolved in methanol (1.23 L) to obtain a clear solution. To this solution, was added 10% Pd—C (15.3 gm, 50% wet) catalyst. The suspension was stirred for 3 hours under 100 psi hydrogen atmosphere at 35° C. As reaction showed completion on TLC (TLC system methanol: chloroform 10:90), the catalyst was filtered through celite under suction. The catalyst was washed with additional methanol (600 ml). The filtrate was evaporated under vacuum below 40° C. to provide a crude residue. The residue was stirred with cyclohexane (1.23 L) for 1 hour. The solid was filtered at suction and the wet cake was washed with additional cyclohexane (0.25 L) to furnish (2S, 5R)-6-hydroxy-7-oxo-2-[((3R)—N-Boc-piperidine-3-carbonyl)-hydrazinocarbonyl]-1,6-diaza-bicyclo[3.2.1]octane (V) in 125 gm quantity as a solid in quantitative yield. The product being unstable was used immediately for the next reaction.

Analysis:
NMR: (CDCl3): 9.0 (br s, 2H), 4.01 (br d, 2H), 3.80 (br s, 1H), 3.74 (br s, 1H), 3.48 (s, 1H), 3.13-3.26 (m, 3H), 2.96 (br s, 1H), 2.47 (br s, 1H), 2.28-2.32 (br dd, 1H), 2.08 (br s, 1H), 1.90-2.0 (m, 3H), 1.65-1.80 (m, 3H) 1.44 (s, 9H).
Mass: (M-1): 410.3 for C18H29N5O6
HPLC purity: 96.34%

Step-3: Preparation of Tetrabutyl ammonium salt of (2S, 5R)-6-sulfooxy-7-oxo-2-[((3R)—N-Boc-piperidine-3-carbonyl)-hydrazinocarbonyl]-1,6-diaza-bicyclo[3.2.1]octane (VI)

A solution of (2S, 5R)-6-hydroxy-7-oxo-2[((3R)—N-Boc-piperidine-3-carbonyl)-hydrazino carbonyl]-1,6-diaza-bicyclo[3.2.1]octane (113 gm, 0.274 mol), in dichloromethane (1.13 L) was charged with triethylamine (77 ml, 0.548 mol) under stirring to provide a clear solution. To the clear solution, was added pyridine sulfur trioxide complex (57 gm, 0.356 mol) under stirring at 35° C. The reaction mixture was stirred for 3 hours. The reaction mixture was worked up by adding 0.5 M aqueous potassium dihydrogen phosphate (1.13 L) followed by ethyl acetate (2.26 L) and the biphasic mixture was stirred for 15 minutes at 35° C. Layers were separated. Aqueous layer was re-extracted with dichloromethane ethyl acetate mixture (1:2 v/v, 2.26 L twice). Layers were separated. To the aqueous layer, was added solid tetrabutyl ammonium hydrogen sulfate (84 gm, 0.247 mol) and stirring was continued for 3 hours at room temperature. Dichloromethane (1.13 L) was added to the reaction mixture. Layers were separated. The aqueous layer was re-extracted with additional dichloromethane (0.565 L). Layers were separated. To the combined organic layer was added silica gel (226 gm) and the suspension was stirred for 1 hour. Suspension was filtered and silica gel was washed with dichloromethane (1 L). The combined filtrate was evaporated under vacuum to provide solid mass. To the solid mass was added cyclohexane (0.9 L) and stirred till complete solidification occurred (about 1 to 2 hours). The suspension was filtered under suction and the wet cake was dried under vacuum below 40° C. to furnish tetrabutyl ammonium salt of (2S, 5R)-6-sulfooxy-7-oxo-2-[((3R)—N-Boc-piperidine-3-carbonyl)-hydrazino carbonyl]-1,6-diaza-bicyclo[3.2.1]octane (VI) as a white solid in 122 gm quantity in 60% yield.

Analysis

NMR: (CDCl3): 8.50 (br s, 2H), 4.32 (br s, 1H), 3.97 (d, 2H), 3.15-3.37 (m, 12H), 2.43 (br s, 1H), 2.33 (d, 1H), 2.10-2.2 (br m, 1H), 1.84-1.95 (m, 3H), 1.60-1.73 (m, 13H), 1.39-1.48 (m, 19H), 0.98 (t, 12H).

Mass: (M-1): 490.4 as a free sulfonic acid for $C_{18}H_{28}N_5O_9S.N(C_4H_9)_4$;

HPLC purity: 96.3%

Step-4: Synthesis of (2S, 5R)-6-sulfooxy-7-oxo-2-[((3R)-piperidine-3-carbonyl)-hydrazinocarbonyl]-1,6-diaza-bicyclo[3.2.1]octane (I)

Tetra-butyl ammonium salt of (2S, 5R)-6-sulfooxy-7-oxo-2-[((3R)—N-Boc-piperidine-3-carbonyl)-hydrazino carbonyl]-1,6-diaza-bicyclo[3.2.1]octane (113 gm, 0.154 mol) was dissolved in dichloromethane (280 ml) and to the clear solution was slowly added trifluoroacetic acid (280 ml) between 0 to 5° C. The reaction mixture was stirred between 0 to 5° C. for 1 hour. The solvent and excess trifluoroacetic acid was evaporated under vacuum below 40° C. to approximately ⅓ of it's original volume to provide pale yellow oily residue. The oily residue was stirred with diethyl ether (2.25 L) for 1 hour to provide a suspension. The precipitate was filtered under suction and transferred to a round bottom flask, to it was added diethyl ether (1.1 L) under stirring. The suspension was stirred for 30 minutes and filtered under suction to provide a solid. The solid was charged in a round bottom flask and to it was added acetone (1.130 L). The pH of suspension was adjusted to 4.5 to 5.5 by adding 10% solution of sodium-2-ethyl hexanoate in acetone carefully. The resulting suspension was filtered under suction and the wet cake was washed with acetone (550 ml) to provide a crude solid. The obtained solid was dried under vacuum below 40° C. to furnish 65 gm of a crude mass. The crude mass was dissolved in water (65 ml) under stirring and to the clear solution was added isopropyl alcohol (455 ml). The suspension was stirred for 24 hours and filtered under suction. The wet cake was washed with isopropyl alcohol (225 ml) and dried under vacuum below 40° C. to provide a crystalline (2S, 5R)-6-sulfooxy-7-oxo-2-[((3R)-piperidine-3-carbonyl)-hydrazino carbonyl]-1,6-diaza-bicyclo [3.2.1]octane (I) free from impurities in 48 gm quantity in 80% yield.

Analysis:

NMR: (DMSO-d6)=9.97 (d, 2H), 8.32 (br s, 2H), 4.00 (br s, 1H), 3.81 (d, 1H), 3.10-3.22 (m, 3H), 2.97-3.02 (m, 2H), 2.86-2.91 (m, 1H), 2.65-2.66 (m, 1H), 1.97-2.03 (m, 1H), 1.57-1.88 (m, 7H).

Mass: (M-1): 390.3 for $C_{13}H_{21}N_5O_7S$

HPLC purity: 95.78%

Specific rotation: $[\alpha]^{25}_D$: −32.6° (c 0.5, water)

X-ray powder diffraction pattern comprising peak at (2 Theta Values): 10.28 (±0.2), 10.57 (±0.2), 12.53 (±0.2), 13.82 (±0.2), 15.62 (±0.2), 18.16 (±0.2), 18.49 (±0.2), 20.35 (±0.2), 20.64 (±0.2), 21.33 (±0.2), 22.99 (±0.2), 23.18 (±0.2), 24.27 (±0.2), 24.81 (±0.2), 25.45 (±0.2), 29.85 (±0.2), 30.45 (±0.2), 32.39 (±0.2), 36.84 (±0.2).

Typical X-ray analysis was performed as follows. Pass the test substance through sieve #100 BSS or gently grind it with a mortar and pestle. Place the test substance uniformly on a sample holder having cavity surface on one side, press the sample and cut into thin uniform film using a glass slide in such a way that the surface of the sample should be smooth and even. Record the X-ray diffractogram using the following instrument parameters.

Instrument: X-Ray Diffractometer (PANalytical, Model X'Pert Pro MPD)

Target source: Cu k (α)

Anti-scattering slit (Incident beam): 1°

Programmable Divergent slit: 10 mm (fixed)

Anti-scattering slit (Diffracted beam): 5.5 mm

Step width: 0.02°

Voltage: 40 kV

Current: 40 mA

Time per step: 30 seconds

Scan range: 3 to 40°

We claim:
1. A compound of Formula (I)

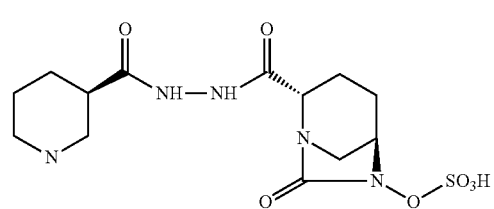

Formula (I)

in a crystalline form, wherein said compound of Formula (I) having a purity of at least about 95% as determined by HPLC, and wherein said crystalline form having an X-ray powder diffraction pattern comprising a peak selected from the group consisting of 10.28 (±0.2), 10.57 (±0.2), 12.53 (±0.2), 13.82 (±0.2), 15.62 (±0.2), 18.16 (±0.2), 18.49 (±0.2), 20.35 (±0.2), 20.64 (±0.2), 21.33 (±0.2), 22.99 (±0.2), 23.18 (±0.2), 24.27 (±0.2), 24.81 (±0.2), 25.45 (±0.2), 29.85 (±0.2), 30.45 (±0.2), 32.39 (±0.2), and 36.84 (±0.2) degrees 2 theta.

2. A compound of Formula (I)

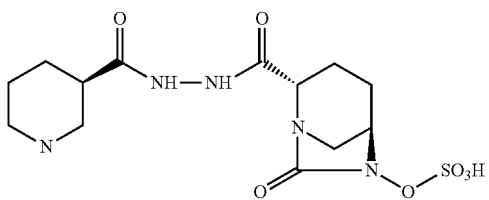

Formula (I)

in a crystalline form, wherein said compound of Formula (I) having a purity of at least about 95% as determined by HPLC, and wherein said crystalline form having an X-ray powder diffraction pattern comprising a peak selected from the group consisting of 10.28 (±0.2), 10.57 (±0.2), 12.53 (±0.2), 13.82 (±0.2), 15.62 (±0.2), 18.16 (±0.2), 18.49 (±0.2), 20.35 (±0.2), 20.64 (±0.2), 21.33 (±0.2), 24.27 (±0.2), 24.81 (±0.2), and 25.45 (±0.2) degrees 2 theta.

3. A pharmaceutical composition comprising the compound of claim 1.

4. A pharmaceutical composition comprising the compound of claim 2.

5. A pharmaceutical composition comprising a compound of Formula (I)

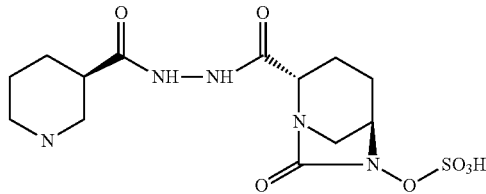

Formula (I)

in a crystalline form, wherein said crystalline form having an X-ray powder diffraction pattern comprising a peak selected from the group consisting of 10.28 (±0.2), 10.57 (±0.2), 12.53 (±0.2), 13.82 (±0.2), 15.62 (±0.2), 18.16 (±0.2), 18.49 (±0.2), 20.35 (±0.2), 20.64 (±0.2), 21.33 (±0.2), 22.99 (±0.2), 23.18 (±0.2), 24.27 (±0.2), 24.81 (±0.2), 25.45 (±0.2), 29.85 (±0.2), 30.45 (±0.2), 32.39 (±0.2), and 36.84 (±0.2) degrees 2 theta.

6. A pharmaceutical composition comprising a compound of Formula (I)

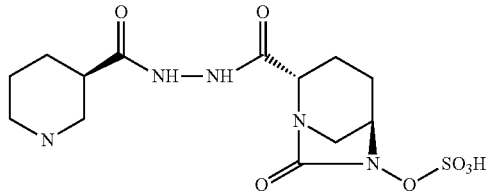

Formula (I)

in a crystalline form, wherein said crystalline form having an X-ray powder diffraction pattern comprising a peak selected from the group consisting of 10.28 (±0.2), 10.57 (±0.2), 12.53 (±0.2), 13.82 (±0.2), 15.62 (±0.2), 18.16 (±0.2), 18.49 (±0.2), 20.35 (±0.2), 20.64 (±0.2), 21.33 (±0.2), 24.27 (±0.2), 24.81 (±0.2), and 25.45 (±0.2) degrees 2 theta.

* * * * *